(12) United States Patent
Nissen

(10) Patent No.: US 6,291,525 B1
(45) Date of Patent: Sep. 18, 2001

(54) METHOD FOR IMPROVING A HUMAN'S PERCEPTION OF HIS EMOTIONAL STATE

(75) Inventor: Steven L. Nissen, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/391,830

(22) Filed: Sep. 8, 1999

(51) Int. Cl.$^7$ .................................................. A61K 31/19
(52) U.S. Cl. ............................................................ 514/557
(58) Field of Search ............................................. 514/557

(56) References Cited

PUBLICATIONS

Mero, A., Sports Medicine, 27/6 (347–358), 1999.*

* cited by examiner

Primary Examiner—Phyllis G. Spivack
(74) Attorney, Agent, or Firm—Leydig, Voit & Mayer, Ltd.

(57) ABSTRACT

The present invention provides a method for improving a human's perception of his emotional state. The method comprises administering β-hydroxy-β-methylbutyric acid to the human in an amount sufficient to improve his perception of his emotional state. The method can further comprise co-administering arginine and glutamine and/or engaging the human in non-resistance training.

21 Claims, 1 Drawing Sheet

METHOD FOR IMPROVING A HUMAN'S PERCEPTION OF HIS EMOTIONAL STATE

TECHNICAL FIELD OF THE INVENTION

The present invention relates to a method for improving a human's perception of his emotional state by administering β-hydroxy-β-methylbutyric acid (HMB) to a human.

BACKGROUND OF THE INVENTION

Mood disorders are the most common serious psychiatric problem facing people today. It has been estimated that during any one-year period, 17.6 million American adults or 10% of the population suffer from a mood disorder, such as a depressive illness. A depressive disorder is a "whole-body" illness, which involves the body, mood, and thoughts. It affects the way one eats and sleeps, the way one feels about oneself, and the way one views the world. Depressive disorders come in different forms, ranging from major depression to a less severe form of depression called dysthymia. Dysthymia involves long-term, chronic symptoms that do not disable, but keep one from operating at full potential or from feeling good. Common symptoms of depressive illness include, among other symptoms: (1) persistent sad, anxious, or "empty" mood; (2) feelings of hopelessness and pessimism; (3) feelings of guilt, worthlessness, and helplessness; (4) loss of interest or pleasure in hobbies that were once enjoyed; (5) decreased energy and increased fatigue; 6) restlessness and irritability; and (7) difficulty in concentrating, remembering, and making decisions.

The cost of depressive disorders, in terms of human suffering, cannot be underestimated. Depressive illnesses interfere with normal functioning and cause significant pain and suffering, not only to those who have the disorder, but also to those who care about them. Furthermore, the economic cost of depressive illness has been estimated to be $30–44 billion a year, with an estimated 200,000,000 lost work days annually and a loss of productivity, due to the nature of depressive symptoms. Possibly the saddest fact about depressive disorders is that much of the suffering is unnecessary. Most people with a depressive illness do not seek treatment, due to the stigma attached with depressive disorders or a lack of access to the health care system.

In view of the foregoing, there exists a need for a method for improving a human's perception of his emotional state, especially a method which involves the use of an over-the-counter dietary supplement. The present invention provides such a method. These and other advantages of the present invention, as well as additional inventive features, will be apparent from the description of the invention provided herein.

BRIEF SUMMARY OF THE INVENTION

The present invention provides a method for improving a human's perception of his emotional state. The method comprises administering HMB to the human in an amount sufficient to improve his perception of his emotional state. The perception of his emotional state can be improved by an enhancement of a pleasant affect and/or by a diminishment of an unpleasant affect. The method can further comprise co-administering arginine and glutamine to the human and/or engaging the human in non-resistance training.

DETAILED DESCRIPTION OF THE INVENTION

Figure 1:
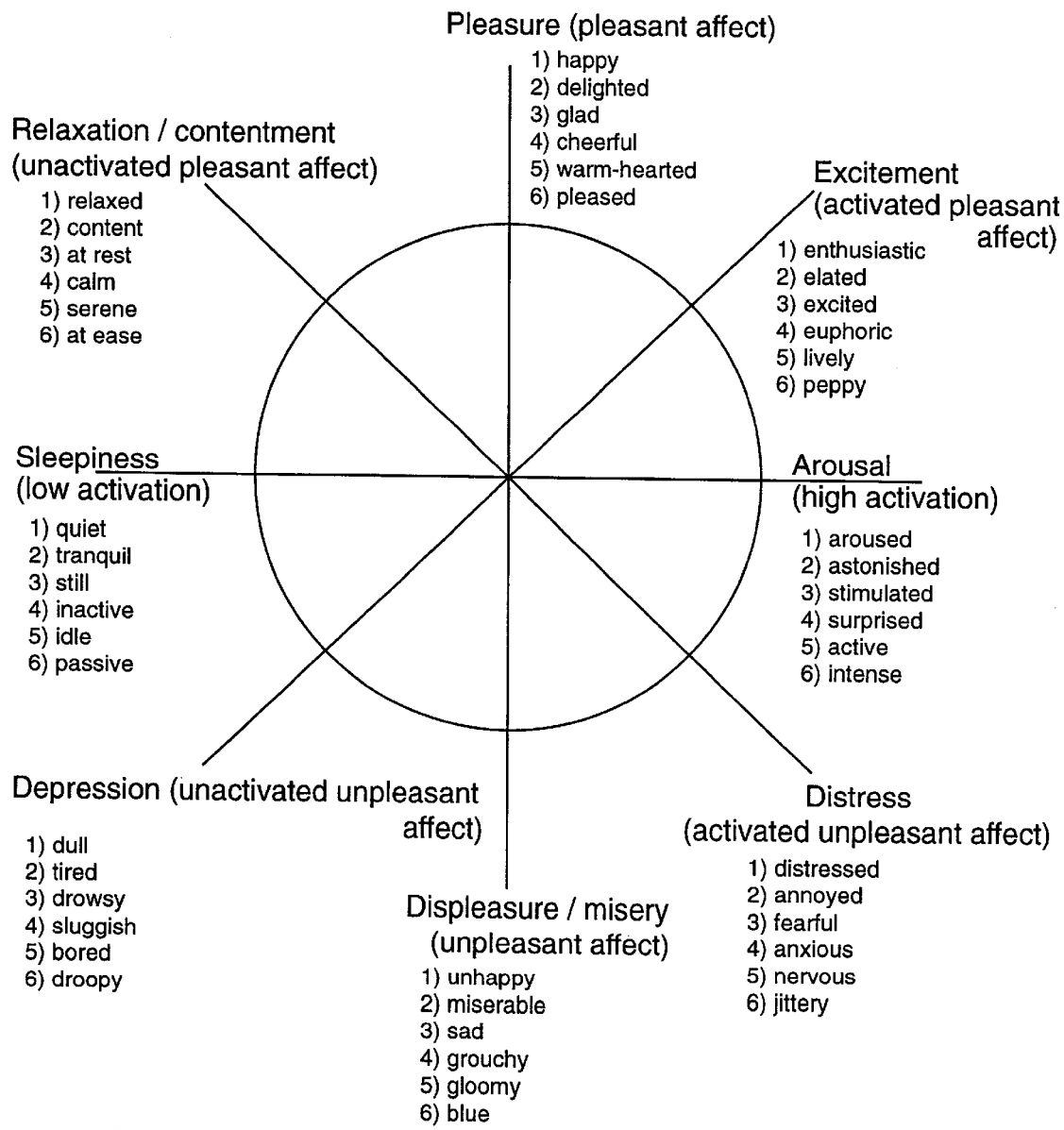
FIG. 1 is a spatial representation of the Circumplex Test of Affect model.

HMB, which is a minor product of the leucine metabolic pathway, has been found to be useful in a variety of applications. Specifically, as described in U.S. Pat. No. 5,360,613 (Nissen), HMB is useful for reducing blood levels of total cholesterol and low-density lipoprotein cholesterol. In U.S. Pat. No. 5,348,979 (Nissen et al.), HMB is described as being useful for promoting nitrogen retention in humans. U.S. Pat. No. 5,028,440 (Nissen) discusses the use of HMB to increase lean tissue development in meat-producing animals. Additionally, HMB has been described as being effective in enhancing the immune response of mammals (U.S. Pat. No. 4,992,470 (Nissen)).

It has now been surprisingly and unexpectedly discovered that HMB can improve a human's perception of his emotional state. In view of this, the present invention provides a method for improving a human's perception of his emotional state. The method comprises administering HMB to the human in an amount sufficient to improve his perception of his emotional state, wherein, upon administration of HMB, the human's perception of his emotional state is improved.

A human's perception of his emotional state can be improved by an enhancement of a pleasant affect. A pleasant affect can include an activated pleasant affect (e.g. excitement), an unactivated pleasant affect (e.g. contentment), and a neutral pleasant affect (e.g. happiness). Emotional states associated with an activated pleasant affect include enthusiasm, excitement, elation, euphoria, liveliness, and peppiness. Emotional states associated with an unactivated pleasant affect include relaxation, contentment, restfulness, serenity, ease, and calmness. Examples of emotional states associated with a neutral pleasant affect include happiness, delight, gladness, cheerfulness, warm heartedness, and pleasure.

Additionally or alternatively, a human's perception of his emotional state can be improved by a diminishment of an unpleasant affect. An unpleasant affect can include an activated unpleasant affect (e.g. anxiety), an unactivated unpleasant affect (e.g. drowsiness), and a neutral unpleasant affect (e.g. sadness). Examples of emotional states associated with an activated unpleasant affect include distress, annoyance, fear, nervousness, jitteriness, and anxiety. Examples of emotional states associated with an unactivated unpleasant affect include dullness, tiredness, drowsiness, sluggishness, boredom, and droopiness. Examples of emotional states associated with a neutral unpleasant affect include unhappiness, sadness, misery, grouchiness, gloominess, and blueness.

HMB, which, in addition to being known as β-hydroxy-β-methylbutyric acid, is also known as β-hydroxy-isovalaryic acid and can be represented in its free-acid form as $(CH_3)_2(OH)CCH_2COOH$. The term "HMB" refers to the compound having the foregoing chemical formula, in both its free acid and salt forms, and derivatives thereof. While any suitable form of HMB can be used within the context of the present invention, preferably, HMB is selected from the group consisting of a free acid, a salt, an ester, and a lactone; more preferably, HMB is a salt.

While any suitable HMB salt can be used within the context of the present invention, preferably, the HMB salt is water-soluble or becomes water-soluble in the stomach or intestines of a human. More preferably, the HMB salt is selected from the group consisting of a sodium salt, a potassium salt, a magnesium salt, a chromium salt, and a calcium salt. Most preferably, the HMB salt is a calcium salt. However, other non-toxic salts, such as other alkali metal or alkaline earth metal salts, can be used. When HMB is to be administered in an ingestible form, it is preferred that the salt be dry, non-sticky, and finely-divided, such as a powder, for blending with liquids and for formulating into a pharmaceutically acceptable form such as a tablet or a capsule.

Similarly, any pharmaceutically acceptable ester can be used in the context of the present invention. Desirably, the HMB ester is rapidly converted to HMB in its free acid form. Preferably, the HMB ester is a methyl or ethyl ester. HMB methyl ester and HMB ethyl ester are rapidly converted to the free acid form of HMB.

Likewise, any pharmaceutically acceptable lactone can be used in the context of the present invention. Desirably, the HMB lactone is rapidly converted to HMB in its free acid form. Preferably, the HMB lactone is an isovalaryl lactone or a similar lactone. Such lactones are rapidly converted to HMB in its free acid form.

Methods for producing HMB and its derivatives are well-known in the art.

For example, HMB can be synthesized by oxidation of diacetone alcohol. One suitable procedure is described by Coffinan et al., *J. Am. Chem. Soc.* 80: 2882–2887 (1958). As described therein, HMB is synthesized by an alkaline sodium hypochlorite oxidation of diacetone alcohol. The product is recovered in free acid form, which can be converted to the desired salt. For example, HMB can be prepared as its calcium salt by a procedure similar to that of Coffman et al. in which the free acid of HMB is neutralized with calcium hydroxide and recovered by crystallization from an aqueous ethanol solution. The calcium salt of HMB is commercially available from Metabolic Technologies, Ames, Iowa.

Any suitable dose of HMB, so as to improve a human's perception of his emotional state, can be used within the context of the present invention. Methods of calculating proper doses of a drug to achieve a desired effect in humans are well-known in the art. The dose of HMB administered to a human can be stated as a function of the total diet of a human, where HMB is administered in an ingestible form, and as a function of the body weight of the human.

Suitable doses of HMB are described below in terms of a preferred form of HMB for illustration purposes. With respect to administering the calcium salt of HMB in an ingestible form, such as a powder, the calcium salt of HMB preferably constitutes from about 0.02 wt. % to about 2.0 wt. %, more preferably, from about 0.2 wt.% to about 1.0 wt. %, and most preferably, about 0.6 wt. % of the total daily diet of the human.

With respect to the dose of the calcium salt of HMB to administer, as a function of the body weight of the animal, it is preferable to administer at least about 5–300 mg of the calcium salt of HMB per kg of body weight per 24 hours, more preferably, at least about 15–140 mg/kg body weight/ 24 hours, and most preferably, at least about 40 mg/kg body weight/24 hours. Under most circumstances, it will usually not be necessary to administer more than 300 mg/kg body weight/24 hours, although higher amounts may be necessary and certainly can be used. Furthermore, the dose of HMB can be administered with any suitable frequency (e.g., one 3 g dose per day or two 1.5 g doses per day) and over any suitable time period (e.g., a single dose can be administered over a 5 minute time period or over a 1 hour time period). Of course, when other forms of HMB, e.g., HMB itself, or other salts and/or derivatives of HMB, are used within the context of the present invention, molar equivalents of the foregoing concentrations are preferably used.

Methods of administering HMB are also well-known in the art, and HMB can be administered in any suitable manner. Preferably, HMB is administered in an ingestible form. When HMB is administered in an ingestible form, HMB is preferably in the form of a liquid drink, in which HMB is mixed as a powder, or a pharmaceutical composition. More preferably, HMB is in the form of a liquid drink in which HMB is mixed as a powder. Any suitable liquid comprising HMB can be utilized within the context of the present invention. In order to prepare HMB as a liquid drink, HMB will normally be blended with the appropriate liquid in such a way that the HMB is substantially uniformly distributed in the liquid. Examples of suitable liquids include water, coffee, tea, and other beverages such as sports drinks, orange drinks, or complete nutritional drinks. Although any suitable pharmaceutical composition comprising HMB can be utilized within the context of the present invention, preferably, HMB is blended with a suitable pharmaceutical carrier, such as dextrose or sucrose, and is subsequently tabulated or encapsulated. Other pharmaceutically acceptable carriers are well-known in the art and include various other starches and saline solutions.

The present inventive method can further comprise co-administering arginine and glutamine. Arginine and glutamine can be isolated from nature or synthesized in accordance with methods known in the art. Preferably, L-isomers of arginine and glutamine are used.

The present inventive method can also further comprise engaging the human in non-resistance training. While any suitable form of non-resistance training can be used within the context of the present invention, preferred forms of non-resistance training include running, walking, sit-ups, and cycling.

In one embodiment of the present invention, the method comprises administering HMB to a human AIDS patient so as to improve his perception of his emotional state. In the context of this embodiment, the improvement of his perception of his emotional state consists of a diminishment of an unpleasant affect.

The method used to evaluate a human's perception of his emotional state is based on the Circumplex Model of Affect (Russell, J. A., J. Person. and Soc. Psych., 39, 1161–1178 (1980)). Affect can be described as a set of dimensions, such as displeasure, distress, depression, excitement, and so on. The Circumplex Model of Affect provides a means to study and categorize affective states, based on the concept that these affective states or dimensions are interrelated in a highly systematic fashion. The interrelationship can be represented by a spatial model in which affective concepts fall in a circle in the following order: pleasure (0°), excitement (45°), arousal (90°), distress (135°), displeasure (180°), depression (225°), sleepiness (270°) and relaxation (315°). This model is depicted in FIG. 1. The Circumplex Model of Affect was developed by performing several studies in which subjects were given a list of 48 descriptive words (e.g. aroused, astonished, excited, delighted, pleased, glad, serene, content, sleepy, tired, depressed, miserable, annoyed, etc.) and instructed to place each word into one of the eight categories of affect (e.g. pleasure, excitement, arousal, distress, displeasure, depression, sleepiness, and relaxation). Next, the subjects were asked to place the eight categories into a circular order in such a way that (1) words opposite each other on the circle describe opposite feelings and (2) words closer together on the circle describe feelings that are more similar. The majority of the responses were organized in the manner represented by the Circumplex Model of Affect. Thus, the model was developed from laymen's perceptions of descriptive words and affective categories, and is currently used as a tool for psychologists to represent the structure of affective experience, as assessed through self-report, and as a representation of the cognitive structure that laymen utilize in conceptualizing affect.

EXAMPLES

The following examples further illustrate the present invention. These examples are not intended to limit the scope of the invention.

Example 1

This example demonstrates the method used to evaluate a human's perception of his emotional state.

Each subject of a study was given a daily dose of either HMB or a placebo. On a weekly basis, the individual subject was administered the Circumplex Test of Affect. Briefly, the test consisted of presenting to each subject 48 words that describe various emotions. An example of the test is presented below. The subject was asked to evaluate his own emotional state in reference to each of the descriptive words. Each word was given a score from 1–5, representative of the degree of accordance between the subject's emotional state and the descriptive word, with 1 being "very slightly" or "not at all"; 2 being "a little"; 3 being "moderately"; 4 being "quite a bit"; 5 being "extremely." The scores for six words composing a particular emotional category (e.g. "activated affect," "unactivated pleasant affect," "pleasant affect," etc.) were then summed to create a score for that emotional category.

Example 2

This example demonstrates that HMB improves a human's perception of his emotional state.

The following studies were performed by administering to each subject a daily dose of either HMB or a placebo and testing his/her emotional profile on a weekly basis. Nine different study groups were tested under various conditions for a time duration which ranged from 3 weeks to 8 weeks. The conditions of each study are described in detail below and the results displayed in Table 1. All studies were double blinded and placebo controlled. Each study was reviewed by the Institutional Review Board and informed consent was obtained for all subjects. Exclusion criteria were ongoing chronic disease process, smoking, illegal drug use and certain age, sex and weight requirements depending on the study.

Study 1:

This 3-week study was conducted at Iowa State University. Twenty-eight male volunteers, between the ages of 19 and 30, were given either 3g HMB/day or a placebo. Subjects exercised by weight-lifting three times per week for three weeks and alternated exercising either the upper or lower body during each weight-lifting session.

Study 2:

This study was carried at Iowa State University in healthy athletes who were subjected to stringent exercise schedules. Twenty-five males between the ages of 19 and 22, weighing between 80 and 130 kg, were studied over a 7-week period. Subjects were supplemented with 3 g of calcium HMB (Ca-HMB) daily contained in the form of a protein shake, which was consumed once in the morning and once in the evening (1.5 g Ca-HMB per shake). Control subjects received an isocaloric carbohydrate drink instead of the protein shake. Subjects exercised a total of six days a week with resistance exercise on five days each week. All subjects ate their normal meals at the athletic training center, and were allowed free access to another protein drink during the workouts.

Study 3:

This 4-week study was conducted at Iowa State University and was mainly designed to document safety of HMB in women. A total of 37 females between the ages of 20 and 41 were used. Subjects were instructed to maintain any exercise program in which they were currently involved, but not to start any new programs during the study. Each subject was instructed to consume 6 oz. of orange juice containing either 1.5 g of Ca-HMB or a placebo, once in the morning and once in the evening.

Study 4:

This 4-week study was conducted at Iowa State University to examine the effect of prior training on the effect of HMB in young males between the ages of 18 and 38. Subjects who were classifed as trained, had a regular resistance exercise program of at least 3 times per week. Untrained subjects did not participate in any regular weight-lifting or other resistance exercise program for at least four months before the study. Thirty-seven subjects were randomly assigned to either 3 g HMB/day or a placebo, given in three divided doses per day. All subjects underwent a supervised resistance training regimen during the 4 week study.

Study 5.

This study was conducted at Iowa State University using 12 male and female volunteers, aged 21–47 years. Subjects were paired according to their best two-mile run time and past running experience. Treatments of either 3.0 g of HMB or a placebo (rice malto-dextrin) supplement were randomly assigned in a double-blind fashion. Subjects took four capsules (1 g HMB or 1 g placebo per serving) three times per day with their meals. After five weeks of supplementation, subjects participated in a 20 km run, which took place on a collegiate cross country course with approximately 4800 meters of hills.

Study 6:

This 4-week study was conducted at Iowa State University under conditions similar to Study 4, except that 38 women subjects between the ages of 19 and 47 were examined. Similar criteria were used to select trained and untrained subjects.

Study 7:

This 8-week study was conducted at Iowa State University using 37 elderly subjects (aged 63–82 years) who were randomly assigned to one of two groups. The supplemented group received 3 g/day of HMB in the form of capsules containing 250 mg of Ca-HMB and the placebo group received 3 g/day of a placebo. Both treatments were administered in a double blind fashion. All subjects underwent strength training 3 times per week for the duration of the study.

Study 8:

This 8-week study was conducted at Wichita State University using twenty-eight individuals, aged 62–79 years, who were recruited from a physical fitness class. Subjects were randomly assigned to one of two groups, of which the supplemented group received 3 g/day of HMB and the placebo group received 3 g/day of a placebo containing rice flour. Both treatments were administered in a double-blind fashion. Subjects participating in the study had no contraindications to exercise and had physician approval to participate. Subjects underwent strength training 2 times per week and walking exercise 3 times per week for the duration of the study.

Study 9:

This 8-week study at Ball State University was conducted 16 untrained males, aged 18–29. Subjects were matched, based on body weights and assigned to one of three groups which received either 0, 38, or 76 mg/kg/day of HMB. Weight-training consisted of 10 different exercises performed 3 days/week, for eight weeks at 80% of the subject's 1-repetition maximum (1RM). The 1RM was re-evaluated every two weeks with workloads adjusted accordingly.

The effects of HMB treatment in each study were determined as follows: The slope and intercept for each subject was calculated for each of the emotional categories. The difference or delta was then calculated over the study for each subject in each of the eight categories. These differences were then analyzed by using a two tailed Student's T-test using values in each study. A pooled weighted average was calculated by pooling all of the subjects' deltas from each of the studies and a weighted change in each category was determined. Another Student's T-test was determined using all of the pooled deltas. Table 1 expresses the net delta change in category score due to HMB supplementation.

These values were calculated by following example: Using the pooled deltas from all studies, the change in Unactivated Unpleasant Affect for the placebo group was −0.23. The change in the HMB-supplemented group was −1.27, thus the net change expressed in the table is −1.04.

The most striking result of the HMB supplementation was a significant decrease in Unactivated Unpleasant Affect which comprises the following terms: dull, tired, drowsy, sluggish, bored and droopy. This category decreased in 6 of the 9 studies indicating an improvement in the subject's perception of energy level. This was accompanied by in some instances a decrease in Low Activation (quiet, tranquill, still. inactive, idle and passive) and in other instances at least a numerical increase in High Activation (aroused, astonished, stimulated, surprised, active and intense). Therefore, HMB supplementation led to a decreased feeling of tiredness which theoretically should result in a feeling of being less bored and more active.

TABLE 1

Effect of HMB on Emotional Profile of Humans:

Summary of changes in emotional state with when consuming HMB as estimated by the Circumplex Test of Emotion. The subjects were asked to rate from 1–5 how they feel relative to the Descriptive words. The six words composing an emotional category were then summed to create a score for each category. The questions were usually asked weekly during the study and the slope and predicted percent change were calculated for each subject and summed by study. The changes are presented as percent change relative to the placebo. So if the placebo score changed 10% and the HMB treatment changed a −10% the net effect of HMB would be a 20% change relative to the placebo.

| Study descriptors | 1/ISU | 2/ISU | 3/ISU | 4/ISU | 5/ISU | 6/ISU | 7/ISU | 8/WSU | 9/BSU |
|---|---|---|---|---|---|---|---|---|---|
| Sex | Male | Male | Female | Male | Male/Female | Female | Male/Female | Male/Female | Male |
| Exercise and/or type of exercise | weight lifting | weight lifting | none | weight lifting | running | weight lifting | weight lifting | weight lifting | weight lifting |
| Age range | 19–30 | 19–22 | 20–41 | 18–38 | 21–47 | 19–47 | 63–82 | 62–79 | 18–29 |
| Placebo = n | 13 | 15 | 19 | 17 | 4 | 18 | 19 | 15 | 5 |
| HMB = n | 15 | 10 | 18 | 20 | 8 | 20 | 18 | 13 | 7 (4)[2] |
| Study length | 3 wk | 7 wk | 4 wk | 4 wk | 5 wk | 4 wk | 8 wk | 8 wk | 8 wk |

| Emotional categories | Descriptive words/category | Net percent change due to HMB supplementation relative to placebo | | | | | | | | Average (weighted) |
|---|---|---|---|---|---|---|---|---|---|---|
| High activation | aroused, astonished, stimulated, surprised, active, intense | 1.23 | 1.41 | 0.33 | −1.30 −0.07 | 1.69 | −1.08 −0.52 | −6.69*** (−0.52) | | −0.25 |
| Activated Pleasant affect | Enthusiastic, elated, excited, suphoric, lively, peppy | 1.85 | 0.46 | 1.78 | −1.08 −0.24 | 1.14 | 0.09 −0.72 | −4.25** (0.11) | | 0.11 |
| Unactivated Pleasant affect | relaxed, content, at rest, calm, serene, at ease | 2.82*** | −1.70 | 1.10 | −2.41 −1.26 | 0.42 | 0.01 −0.70 | −3.66 (−2.58) | | −0.36 |
| Pleasant affect | happy, delighted, glad, cheerful, warmhearted, pleased | 2.73 | 0.62 | 1.70 | −1.36 0.05 | 1.67 | 0.61 −1.56 | −2.97 (−1.25) | | 0.30 |
| Low activation | quiet, tranquil, still, inactive, idle, passive | 1.78 | −5.14** | −0.34 | −0.88 1.59 | 1.55 | −0.17 −1.78 | −4.22 (−2.17) | | −0.62 |
| Unactivated, unpleasant affect | dull, tired, drowsy, sluggish, bored, droopy | 0.40 | −2.97 | −3.78** | 0.45 −1.06 | 0.75 | −0.61 −2.63* | −1.17 (−2.97) | | −1.04*** |
| Unpleasant | unhappy, miserable, sad, grouchy, gloomy, blue | −0.11 | 0.68 | −1.00 | 1.31 0.68 | 1.14** | −0.02 −1.44 | −1.78 (−1.54) | | 0.05 |
| Activated unpleasant affect | distressed, annoyed, fearful, nervous, jittery, anxious | 0.08 | 0.57 | −1.16 | 0.80 −0.69 | 0.88 | 0.45 −1.62 | −1.72 (−4.67) | | −0.12 |

[1]Sites of the studies were ISU—Iowa State University, WSU—Wichita State University, BSU—Ball State University.
[2]The number in parenthesis is the effect at 6 g/day. These numbers were not included in the average calculation which only consisted of data on 3 g/day.
*significant .05 < p < .09,
**significant p < .05, and
***significant p < .01.
***Indicates a significant effect (p < .05) across all experiments as determined by a weighted t-test.

Example 3

This example demonstrates that the administration of HMB, arginine and glutamine improves a human's perception of his emotional state.

Thirty-four males between the ages of 18 and 37 were each administered in a double-blinded study a daily dosage of either HMB/Arg/Gln (3 grams HMB, 14 grams arginine and 14 grams glutamine) or a placebo. The subjects consumed the mixtures for 4 weeks and emotional profiles were tested on a weekly basis. During the 4-week study, approximately half of the subjects underwent an exercise program, while the other half continued a sedentary lifestyle. The effects of administering HMB in combination with arginine and glutamine were determined by using the methods described in Example 1. The results of the study, reported as the net actual change in the rating scale due to HMB/Arg/Gln for each category showed a 0.71 increase in the "high activation" category; an increase of 1.50 in the "activated pleasant" affect category; an increase of 0.41 in the "unactivated pleasant" affect category; a difference of −0.25 in the "pleasant" affect category; a decrease of 1.80 in the "low activation" category; a difference of 0.20 in the "activated unpleasant" affect category; a decrease of 1.86 in the "unactivated unpleasant" affect category; and a decrease of 1.67 in the "unpleasant" affect category. It should be noted that, in both of the training and non-training groups, there was an overall improvement in the "pleasant" affects and decrease in the "unpleasant" affects.

These results demonstrate that the administration of HMB, in combination with arginine and glutamine, improves a human's perception of his emotional state by enhancing the pleasant affects and diminishing the unpleasant affects.

Example 4

This example demonstrates that the administration of HMB, arginine and glutamine improves a human AIDS patient's perception of his emotional state.

Thirty-eight males and 5 females between the ages of 25 and 53 were each administered in a double blinded study a daily dosage of either HMB/Arg/Gln (3 grams HMB, 14 grams arginine and 14 grams glutamine) or a placebo. The subjects consumed the mixtures for 8 weeks and emotional profiles were tested every 2 weeks during that time. The study group did not participate in an exercise program. The effects of administering HMB in combination with arginine and glutamine were determined by using the methods described in Example 1. The results of the study, reported as the net actual change in the rating scale due to HMB/Arg/Gln for each category, showed a 0.69 decrease in the "high activation" category; a 0.99 decrease in the "activated pleasant" affect category; a decrease of 0.42 in the "unactivated pleasant affect" category; a 0.66 decrease in the "pleasant" affect category; a decrease of 0.88 in the "low activation" category; a decrease of 2.03 in the "activated unpleasant" affect category; a decrease of 1.12 in the "unactivated unpleasant" affect category; and a decrease of 0.82 in the "unpleasant" affect category. It is noteworthy that there was a much greater (almost 2-fold) decrease in "unpleasant" feelings with the mixture compared with the decrease in "pleasant" feelings. This indicates an overall improvement in "pleasant" feelings with the HMB/Arg/Gln mixture.

These results demonstrate that the administration of HMB, in combination with arginine and glutamine, improves an AIDS patient's perception of his emotional state by diminishing the unpleasant affects.

All of the references cited herein, including patents, patent applications and publications, are hereby incorporated in their entireties by reference.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

What is claimed is:

1. A method for improving a human's perception of his or her emotional state, based on the Circumplex Test of Affect, which method comprises administering β-hydroxy-β-methylbutyric acid (HMB) to said human in an amount sufficient to improve his or her perception of his or her emotional state, whereupon said human's perception of his or her emotional state is improved.

2. The method of claim 1, wherein said method further comprises co-administering arginine and glutamine.

3. The method of claim 1, further comprising engaging said human in non-resistance training.

4. The method of claim 2, further comprising engaging said human in non-resistance training.

5. The method of claim 1, wherein the human's perception of his emotional state is improved by an enhancement of a pleasant affect.

6. The method of claim 1, wherein the human's perception of his emotional state is improved by a diminishment of an unpleasant affect.

7. The method of claim 1, wherein said amount is the molar equivalent of at least 0.04 g of the calcium salt of HMB per kg of body weight of said human per 24 hours.

8. The method of claim 2, wherein said amount is the molar equivalent of at least 0.04 g of the calcium salt of HMB per kg of body weight of said human per 24 hours.

9. The method of claim 3, wherein said amount is the molar equivalent of at least 0.04 g of the calcium salt of HMB per kg of body weight of said human per 24 hours.

10. The method of claim 4, wherein said amount is the molar equivalent of at least 0.04 g of the calcium salt of HMB per kg of body weight of said human per 24 hours.

11. The method of claim 2, wherein said arginine and said glutamine are each administered in an amount of at least about 0.18 g per kg of body weight of said human per 24 hours.

12. The method of claim 4, wherein said arginine and said glutamine are each administered in an amount of at least about 0.18 g per kg of body weight of said human per 24 hours.

13. The method of claim 1, wherein said HMB is in a form selected from the group consisting of a free acid, a salt, an ester, and a lactone.

14. The method of claim 13, wherein said salt is selected from the group consisting of a sodium salt, a potassium salt, a magnesium salt, a chromium salt, and a calcium salt.

15. The method of claim 14, wherein said salt is a calcium salt.

16. The method of claim 13, wherein said ester is selected from the group consisting of a methyl ester and an ethyl ester.

17. The method of claim 16, wherein said lactone is isovalaryl lactone.

18. The method of claim 1, wherein said HMB is administered to said human in an ingestible form.

19. The method of claim 18, wherein said ingestible form is a liquid drink in which HMB is mixed as a powder.

20. The method of claim 18, wherein said HMB is administered to said human in a pharmaceutical form.

21. The method of claim 1, wherein said human has AIDS.

* * * * *